US012620146B2

(12) United States Patent
Baykaner et al.

(10) Patent No.: US 12,620,146 B2
(45) Date of Patent: May 5, 2026

(54) GRAPH CONSTRUCTION AND VISUALIZATION OF MULTIPLEX IMMUNOFLUORESCENCE IMAGES

(71) Applicant: AstraZeneca AB, Södertälje (SE)

(72) Inventors: Khan Richard Baykaner, Cambridge (GB); Christopher Erik Marino Innocenti, Mölndal (SE); Michael Joseph Surace, Gaithersburg, MD (US); Laura Dillon, Gaithersburg, MD (US)

(73) Assignee: AstraZeneca AB, Södertälje (SE)

( * ) Notice: Subject to any disclaimer, the term of this patent is extended or adjusted under 35 U.S.C. 154(b) by 128 days.

(21) Appl. No.: 18/261,055

(22) PCT Filed: Jan. 11, 2022

(86) PCT No.: PCT/EP2022/050396
§ 371 (c)(1),
(2) Date: Jul. 11, 2023

(87) PCT Pub. No.: WO2022/152672
PCT Pub. Date: Jul. 21, 2022

(65) Prior Publication Data
US 2024/0070940 A1 Feb. 29, 2024

Related U.S. Application Data

(60) Provisional application No. 63/199,608, filed on Jan. 12, 2021.

(51) Int. Cl.
*G06T 11/20* (2006.01)
*G06F 3/04817* (2022.01)
(Continued)

(52) U.S. Cl.
CPC ........ *G06T 11/203* (2013.01); *G06F 3/04817* (2013.01); *G06T 7/62* (2017.01);
(Continued)

(58) Field of Classification Search
CPC .................... G06T 11/203; G06T 7/62; G06T 2207/10064; G06F 3/04817; G06F 18/29;
(Continued)

(56) References Cited

U.S. PATENT DOCUMENTS

| | | | |
|---|---|---|---|
| 2020/0105421 A1* | 4/2020 | Glushakov .......... | G06F 16/9038 |
| 2020/0184643 A1 | 6/2020 | Coudray et al. | |

(Continued)

FOREIGN PATENT DOCUMENTS

| | | |
|---|---|---|
| JP | 2019-527068 A | 9/2019 |
| JP | 2020-527946 A | 9/2020 |

OTHER PUBLICATIONS

Hamilton, Will, Zhitao Ying, and Jure Leskovec. "Inductive representation learning on large graphs." Advances in neural information processing systems 30 (2017). (Year: 2017).*
(Continued)

*Primary Examiner* — William A Beutel
(74) *Attorney, Agent, or Firm* — Lee Sullivan Shea & Smith LLP

(57) ABSTRACT

Provided herein are system, apparatus, article of manufacture, method and/or computer program product embodiments, and/or combinations and sub-combinations thereof, for providing interactive exploration and analysis of cellular environments represented within MIF images. An embodiment includes a pipeline configured to generate an interactive visualization with selectable icons that represent cells in an MIF image by identifying identifying cells in the MIF image and generating a graph of the MIF image based on coordinates and the properties of the identified cells, with
(Continued)

each node in the graph corresponding to the cells as well as neighboring cells. The graph may be transformed into embeddings and generating an interactive visualization of the graph based on the embeddings. Selectable icons in the interactive visualization correspond to nodes in the graph.

20 Claims, 6 Drawing Sheets

(51) Int. Cl.
| | | |
|---|---|---|
| *G06T 7/62* | (2017.01) | |
| *G06V 20/69* | (2022.01) | |
| *G16H 50/20* | (2018.01) | |

(52) U.S. Cl.
CPC ........... *G06V 20/695* (2022.01); *G16H 50/20* (2018.01); *G06T 2207/10064* (2013.01)

(58) Field of Classification Search
CPC ...... G06V 20/695; G06V 10/82; G06V 20/69; G16H 50/20
See application file for complete search history.

(56) References Cited

U.S. PATENT DOCUMENTS

| | | | | |
|---|---|---|---|---|
| 2022/0164946 | A1* | 5/2022 | Pati | ......................... G16H 10/40 |
| 2023/0170050 | A1* | 6/2023 | Cooper | ................. G16B 40/20 706/21 |

OTHER PUBLICATIONS

Jimenz-Sanchez et al., Unsupervised Learning of Contextual Information in Multiplex Immunofluorescence Tissue Cytometry, 2020

IEEE 17th International Symposium On Biomedical Imaging (ISBI), Apr. 3, 2020, pp. 1275-1279.

International Search Report and Written Opinion for International Application No. PCT/EP2022/050396, mailed Apr. 11, 2022, 10 Pages.

International Preliminary Report on Patentability for International PCT Application No. PCT/EP2022/050396, mailed on 041 Jul. 2023, 8 Pages.

JP Office Action, JP Application No. 2023-541733, Dec. 9, 2025.

Ravindra, Neal G. et al., "Disease State Prediction from Single-Cell Data Using Graph Attention Networks", ACM CHIL 2020, Proceedings of the ACM Conference on Health, Inference, and Learning, https://doi.org/10.1145/3368555.3384449, Apr. 2, 2020, pp. 121-130.

Levy, Joshua et al., "Topological Feature Extraction and Visualization of Whole Slide Images Using Graph Neural Networks", Pacific Symposium on Biocomputing 2021, https://doi.org/10.1142/9789811232701_0027, Nov. 2020, pp. 285-296.

Wu, Duoduo et al., "Comparison Between UMAP and t-SNE for Multiplex-Immunofluorescence Derived Single-Cell Data from Tissue Sections", bioRxiv, https://doi.org/10.1101/549659, Feb. 15, 2019, 37 pages.

Communication Pursuant to Article 94(3) EPC, EP Application No. 22701161.6, dated Jan. 22, 2026, 7 pages.

Schapiro, Denis et al., "histoCAT: Analysis of Cell Phenotypes and Interactions in Multiplex Image Cytometry Data", Nature Methods, vol. 14, No. 9, Sep. 1, 2017, pp. 873-876.

Schapiro, Denis et al., "histoCAT: Analysis of Cell Phenotypes and Interactions in Multiplex Image Cytometry Data, Supplementary Information", Nature Methods, vol. 14, No. 9, Aug. 7, 2017, pp. 1-39, Retrieved from the Internet: URL:https://static-content.springer.com/esm/art%3A10.1038%2Fnmeth.4391/MediaObjects/41592_2017_BFnmeth4391_MOESM1_ESM.pdf.

* cited by examiner

Figure 1:
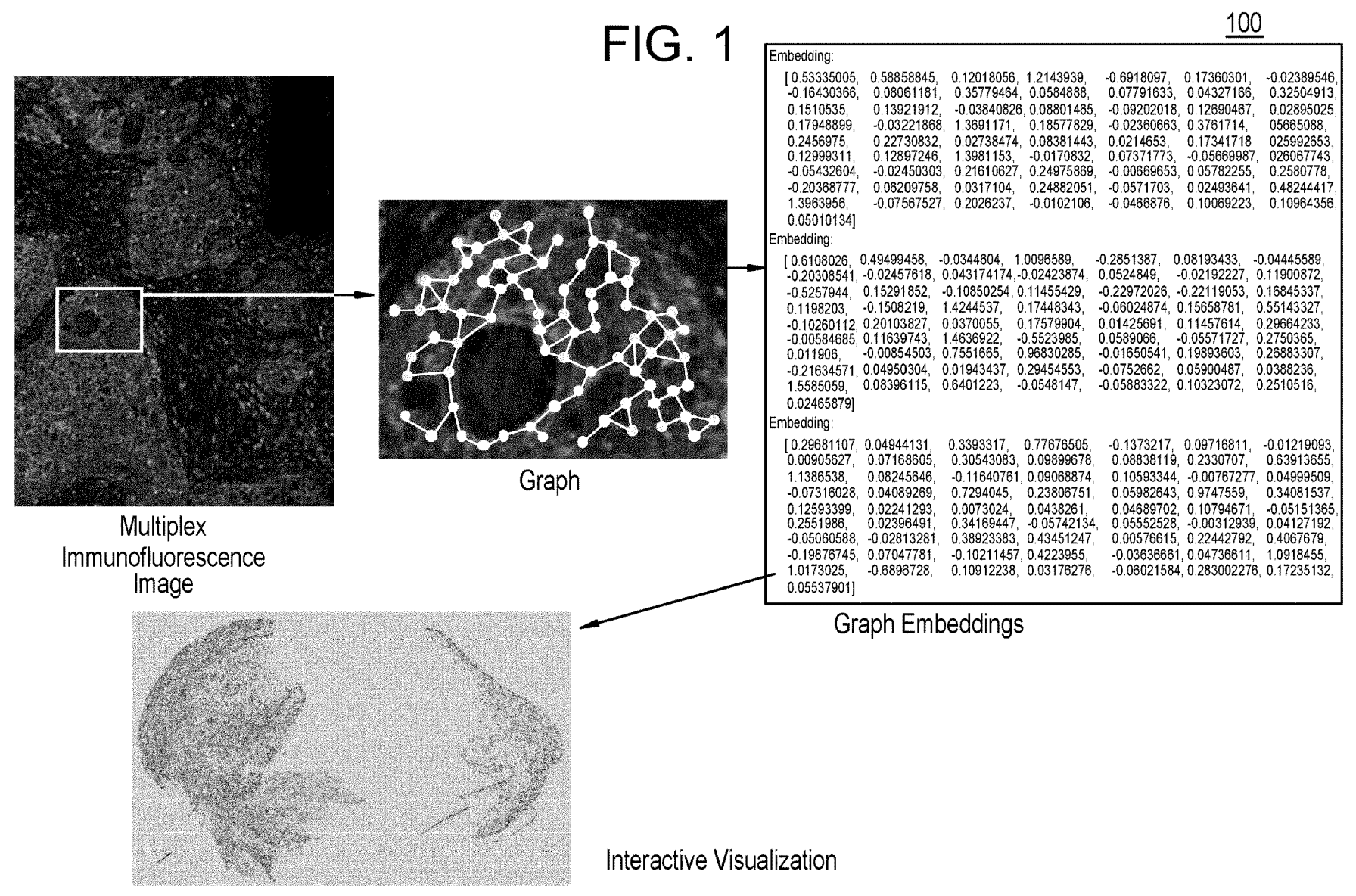

Embedding:
[0.53335005, 0.58858845, 0.12018056, 1.2143939, -0.6918097, 0.17360301, -0.02389546,
-0.16430366, 0.08061181, 0.35779464, 0.0584888, 0.07791633, 0.04327166, 0.32504913,
0.1510535, 0.13921912, -0.03340826, 0.08801465, -0.09202018, 0.12690467, 0.02895025,
0.17948899, -0.03221868, 1.3691171, 0.18577829, -0.02360663, 0.3761714, 05665088,
0.2456975, 0.22730832, 0.02738474, -0.00381443, 0.0214653, 0.17341718, 025992653,
0.12999311, 0.12897246, 1.3981153, -0.0170832, 0.07371773, -0.05669987, 026067743,
-0.05432604, -0.02450303, 0.21610627, 0.24975869, -0.00669653, 0.05782255, 0.2580778,
-0.20368777, 0.06209758, 0.0317104, 0.24882051, -0.0571703, 0.02493641, 0.48244417,
1.3963956, -0.07567527, 0.2026237, -0.0102106, -0.0466876, 0.10069223, 0.10964356,
0.05010134]
Embedding:
[0.6108026, 0.49499458, -0.0344604, 1.0096589, -0.2851387, 0.08193433, -0.04445589,
-0.20308541, -0.02457618, 0.043174174, -0.02423874, 0.0524849, -0.02192227, 0.11900872,
-0.5257944, 0.15291852, -0.10850254, 0.11455429, -0.22972026, -0.22119053, 0.16845337,
0.1198203, -0.1508219, 1.4244537, 0.17448343, -0.06024874, 0.15658781, 0.55143327,
-0.10260112, 0.20103827, 0.0370055, 0.17579904, 0.01425691, 0.11457614, 0.29664233,
-0.00584685, 0.116339743, 1.4636922, -0.55233985, 0.0589066, -0.05571727, 0.27503365,
0.011906, -0.00854503, 0.7551665, 0.96830285, -0.01650541, 0.19893603, 0.26883307,
-0.21634571, 0.04950304, 0.01943437, 0.29454553, -0.0752662, 0.05900487, 0.0388236,
1.5585059, 0.08396115, 0.6401223, -0.0548147, -0.05883322, 0.10323072, 0.2510516,
0.024665879]
Embedding:
[0.29681107, 0.04944131, 0.3393317, 0.77676505, -0.1373217, 0.09716811, -0.011219093,
0.00905627, 0.07168605, 0.30543083, 0.09899678, 0.08838119, 0.2330707, 0.63913655,
1.1386538, 0.082455646, -0.11640761, 0.09068874, 0.105933344, -0.00767277, 0.04999509,
-0.07316028, 0.04089269, 0.7294045, 0.23806751, 0.05982643, 0.9747559, 0.34081537,
0.12593399, 0.02241293, 0.0073024, 0.043826l, 0.04669702, 0.10794671, -0.051151365,
0.2551986, 0.02396491, 0.34169447, -0.05742134, 0.05552528, -0.00312939, 0.04127192,
-0.05060588, -0.02813281, 0.38923383, 0.43451247, 0.00576615, 0.22442792, 0.4067679,
-0.19876745, 0.07047781, -0.10211457, 0.4223955, -0.03636661, 0.04736611, 1.0918455,
1.0173025, -0.6896728, 0.10912238, 0.03176276, -0.06021584, 0.283002276, 0.17235132,
0.05537901]

Graph Embeddings

Graph

Multiplex Immunofluorescence Image

Interactive Visualization

Figure 3:
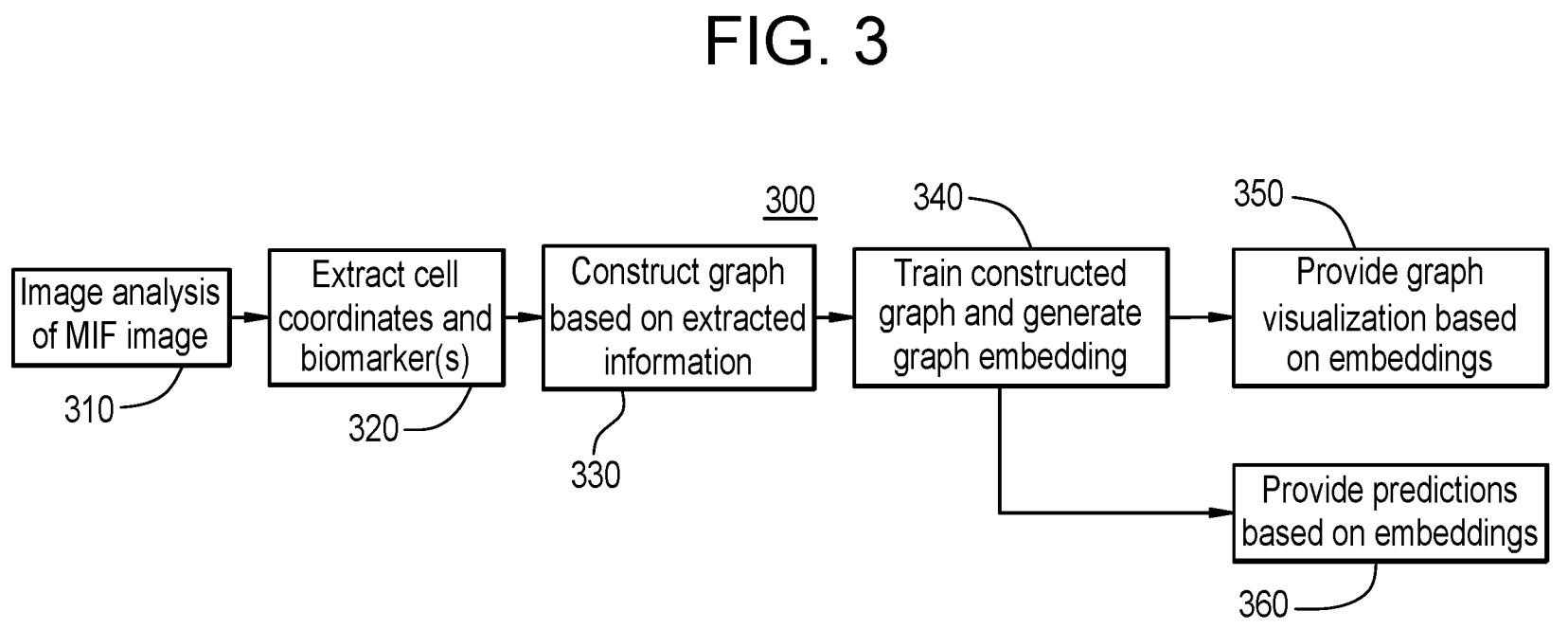

310 — Image analysis of MIF image

320 — Extract cell coordinates and biomarker(s)

330 — Construct graph based on extracted information

340 — Train constructed graph and generate graph embedding

350 — Provide graph visualization based on embeddings

360 — Provide predictions based on embeddings

400A

Interactive Visualization 410

Graph Queries
411

Filtering
412

Embeddings Plot/Graph
413

Neighborhood Graphs
414

Statistical Summaries
415

FIG. 4B

GRAPH CONSTRUCTION AND VISUALIZATION OF MULTIPLEX IMMUNOFLUORESCENCE IMAGES

CROSS-REFERENCE TO RELATED APPLICATIONS

This application is a U.S. National Stage application of International Application No. PCT/EP2022/050396, filed on Jan. 11, 2022, said International Application No. PCT/EP2022/050396 claims benefit under 35 U.S.C. § 119 (e) of the U.S. Provisional Application No. 63/199,608, filed Jan. 12, 2021. International Application No. PCT/EP2022/050396 is incorporated by reference herein in its entirety for all purposes.

FIELD

This disclosure is generally directed to constructing graph representations of multiplex immunofluorescence images for interactively exploring cellular relationships within the multiplex immunofluorescence images as well as for generating predictions regarding treatment outcomes and treatment efficacy.

BACKGROUND

Multiplex immunofluorescence (MIF) is a molecular histopathology tool for the detection of antigens in biological samples using labelled antibodies. MIF has emerged as a useful tool for enabling simultaneous detection of biomarker expression in tissue sections and providing insight into cellular composition, function, and interactions. One benefit of MIF is the capture of complex and broad information about the cells within a cellular environment. While the depth and breadth of the data provided by an MIF image is useful, the sheer complexity and amount of data present challenges for interpretation and visualization. In other words, analyzing the data in an MIF image can be an arduous task.

SUMMARY

Cellular environments are notoriously complex. They may include millions of cells and many different types of cells. Each of these cells may have hundreds of potential interactions. Analysis of biomarker expression in MIF images provide a helpful starting point in analyzing the cells and these interactions but given the number of cells involved, manual analysis of MIF images is practically impossible. Techniques described in this disclosure translate the data provided by MIF images into an intuitive graphical format where cells within MIF images can be manipulated, filtered, queried, and utilized for associated medical predictions.

Provided herein are system, apparatus, article of manufacture, method and/or computer program product embodiments, and/or combinations and sub-combinations thereof, for providing interactive exploration and analysis of cellular environments represented within MIF images.

In some non-limiting embodiments, the system may be a pipeline implemented within a general-purpose computing device or a more dedicated device for image analysis and data visualization. The system may include a memory and/or a non-transitory computer-readable storage device, having instructions stored therein. When executed by at least one computer processor, various operations may be performed, locally or remotely, to analyze an MIF image and generate an interactive visualization representative of the cells within the MIF image. With the implementation of the techniques disclosed herein, the interactive visualization provides an interface for manipulating data associated with the cells in the MIF image. In this way, data within an MIF image can be processed to reveal cellular insights within the image that were not previously possible through conventional analysis. The interactive visualization depicts those insights in a way that medical providers can conduct hypothesis and data-driven research which can lead to more accurate diagnoses of diseases, more accurate predictions of medical outcomes and responses to treatment, and a better understanding of how cells react to current treatments.

An embodiment is directed to system, apparatus, article of manufacture, method and/or computer program product embodiments, and/or combinations and sub-combinations thereof, for generating an interactive visualization with selectable icons that represent cells in an MIF image. These embodiments may include identifying cells in the MIF image. Each of the cells may be associated with coordinates and properties. The embodiments may further include generating a graph of the MIF image based on the coordinates and the properties, wherein the graph includes nodes that correspond to the cells as well as neighboring cells. The graph may further include edges that connect the nodes and also encode properties about each cell such as information about neighboring cells around that cell. The embodiments may further include transforming the graph into embeddings, which are mathematical vector representations of the graph including the nodes, the edges, and the properties. The embodiments may further include providing an interactive visualization of the graph based on the embeddings.

It is to be appreciated that the Detailed Description section below, not the Summary or Abstract sections, is intended to be used to interpret the claims. The Summary and Abstract sections may set forth some, but not all, possible example embodiments of the enhanced densification techniques described herein for providing an interactive visualization of MIF data, and therefore are not intended to limit the appended claims in any way.

BRIEF DESCRIPTION OF THE DRAWINGS

The accompanying drawings are incorporated herein and form a part of the specification.

FIG. 1 illustrates an overview of an example implementation, according to some embodiments.

FIG. 3 illustrates an example method for providing an interactive visualization of a multiplex immunofluorescence image, according to some embodiments.

FIG. 4B illustrates an example process flow for generating a cellular neighborhood plot from an interactive visualization of a multiplex immunofluorescence image, according to some embodiments.

In the drawings, like reference numbers generally indicate identical or similar elements. Additionally, generally, the leftmost digit(s) of a reference number identifies the drawing in which the reference number first appears.

DETAILED DESCRIPTION

Figure 2A:
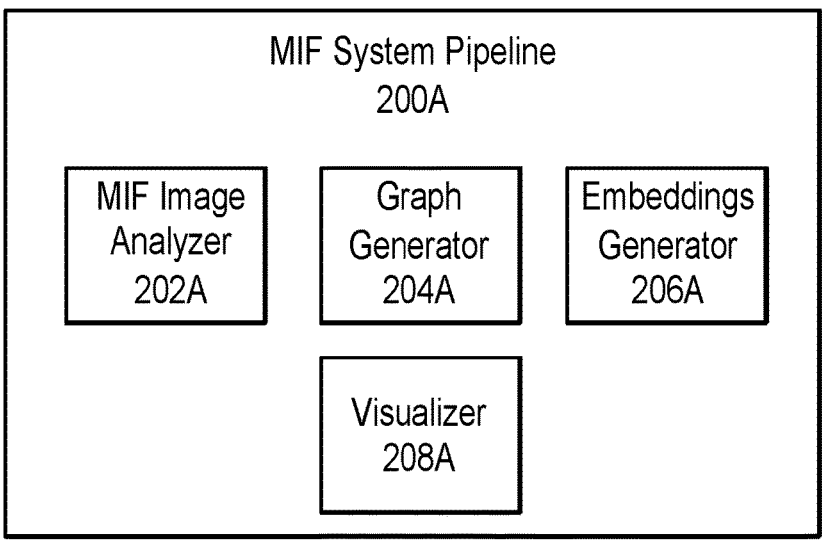
FIG. 2A illustrates an example multiplex immunofluorescence image system pipeline for processing a multiplex immunofluorescence image, according to some embodiments.

The following Detailed Description of the present disclosure refers to the accompanying drawings that illustrate exemplary embodiments consistent with this disclosure. The exemplary embodiments will fully reveal the general nature of the disclosure so that others can, by applying knowledge of those skilled in relevant art(s), readily modify and/or adapt for various applications such exemplary embodiments, without undue experimentation, without departing from the spirit and scope of the disclosure. Therefore, such adaptations and modifications are intended to be within the meaning and plurality of equivalents of the exemplary embodiments based upon the teaching and guidance presented herein. It is to be understood that the phraseology or terminology herein is for the purpose of description and not of limitation, such that the terminology or phraseology of the present specification is to be interpreted by those skilled in relevant art(s) in light of the teachings herein. Therefore, the detailed description is not meant to limit the present disclosure.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

FIG. 1 is a diagram of an overview of an example process flow 100. As described herein, example process flow 100 merely provides a general discussion of features for providing an interactive visualization of MIF image data. While the following discussion discusses interactive visualization in the context of MIF and MIF image data, the interactive visualization may be based on other types of image data that provide cellular information, such as multiplex immunohistochemistry (MIHC) image data and mass spectrometry imaging. Accordingly, the discussion below with regard to the processing an MIF image to produce a graph and embeddings and subsequently generating an interactive visualization may also apply to processing image data from MIHC and mass spectrometry images. More details of the process and the interactive visualization are discussed with respect to FIGS. 2-4 below.

As shown in FIG. 1, example process flow 100 may start with an MIF image. The cellular environment in an MIF image is typically very complex and the information provided by the biomarker expression of MIF results in large data sets to interpret. Process flow 100 describes transforming the MIF image into a visualization that allows those data sets to be manipulated and utilized in a more automated manner. Process flow 100 may involve analyzing the MIF image to identify data points associated with the cellular environment in the image. In an embodiment, the analysis may include identifying tissue cells in the MIF image and segmenting the identified tissue cells into biologically meaningful regions. Examples of such biologically meaningful regions include a tumor center and tumor stroma.

Examples of functions for performing the segmenting step may include random forest classifiers based on training regions. For example, cell segmentation may include identifying round objects of the predetermined size and having an eccentricity with sufficient contrast in the nuclear biomarker channel. As another example, the Voronoi watershed may be used to estimate the cell membrane and cytoplasm of the cells in the MIF image; membrane biomarkers may be used to refine these estimates. Biomarker positivity is generally assessed by integrating the intensity of each channel across the cell area or subcellular compartment.

The result of the MIF analysis is information regarding the data points on the image indicative of the cellular environment such as cellular location, cell phenotype (which may be considered a combination of biomarkers associated with the cell), cell-cell relationships, and immunofluorescence intensities. Biomarkers used for MIF can include molecules measurable on or within cells that can be used to characterize the cell or tissue. For example, the expression of certain biomarkers may be indicative of the identity, function, or activity of a cell. Different diseases (cancer, heart disease) may be associated with biomarkers which may be used to diagnose the disease and responses to medical treatments may cause changes in biomarker expression. Examples of biomarkers include DNA or proteins.

The positioning information may be stored in a tabular format that describes the coordinates and phenotypes of each cell identified in the MIF image. Positioning of cells may be based on the centroid of a nucleus or the whole cell. In an embodiment, positioning may be implemented as cell X/Y coordinates on a whole slide coordinate system. The image information may be recorded in a log file and may be used for the next step in process flow 100, which is graph construction.

A graph may be constructed based on the image information. For example, this step may involve extracting cell positions (X/Y coordinates) from the log file and extracting biomarker information such as immunofluorescence intensities of each cell. Other examples of biomarker information include auxiliary features such as cell diameter, cell area, and cell eccentricity. The graph may be constructed based on this extracted information by performing a pairwise identification of cells. In an embodiment, a selectable distance threshold may be used to identify cell pairs. Identified pairs that are within the selectable distance threshold may be connected in the graph by an edge. The graph is constructed when all pairs of cells have been identified and added to the graph as nodes connected by an edge. Accordingly, the constructed graph is composed of nodes corresponding to cells depicted in the MIF image as well as edges connecting certain nodes. The edges correspond to the selectable distance threshold between any nodes within the graph.

Once the graph is constructed, the next step in process flow 100 involves transforming the graph into graph embeddings, which are numeric vectors or feature vectors that represent the information encoded in the constructed graph. Embeddings may represent numerically, for example, within a matrix, the properties or features of the constructed graph in a vector space where nearby embeddings represent similar nodes, edges, and sub-graphs. Hence, embeddings may capture information about the graph in various forms of granularity including the nodes of the graph, edges of the graph, and sub-graphs of the entire graph.

Embeddings may represent information about each cell represented as nodes in the graph such as the cell's location, immunofluorescence intensity, cell phenotype, and the cell's neighborhood. A cell's neighborhood may be centered around the node (that corresponds to that cell) and any surrounding nodes (corresponding to nearby cells as depicted in the MIF image) that are within a certain number of hops from the center node. Embeddings may also be trained to more accurately represent the cell information or the neighborhood information.

Embeddings may be generated via a graph training algorithm in order to learn nodes and edges within the graph. Application of a graph training algorithm may include the initial steps of selecting the number of hops (to determine the neighborhood size) and selecting the embedding size or type of embedding output. In some embodiments, the graph training algorithm is unsupervised. Examples of this include deep graph infomax (DGI) and GraphSAGE. The size of an embedding represents the amount of information of the graph that may be captured by the embedding. The larger the embedding size, the more information can be represented in the embedding space and hence potentially more information from the graph may be captured by the embedding. Types of embedding output include node embeddings, edge embeddings, a hybrid of both node and edge embeddings, subgraph embeddings, and whole graph embeddings, just to name a few examples.

Converting the graph into a vector representation provides a number of advantages. Data in graphs are not easily manipulated because they consist of edges and nodes. This composition also reduces the efficacy of machine learning algorithms. In comparison, vector representations are easier to manipulate and have a larger selection of machine learning algorithms that may be applied to them.

After generation of the graph embeddings, process flow 100 next generates the interactive visualization based on information in the graph embeddings. The interactive visualization is a tool for exploring information encoded in the embeddings. In an embodiment, the interactive visualization provides a two-dimensional visual projection of the embeddings. A scatterplot is one example of such a two-dimensional projection. Nodes of the interactive visualization may be manipulated in a variety of ways such as cell selection, biomarker filtering, or neighborhood plotting, just to name a few examples, which allows for a number of real-life diagnostic benefits including clustering nodes for specific patients, identifying patients (based on their nodes) that responded to therapy, and generating predictions for how a patient may respond to a therapy (based on extrapolating data based on the nodes).

The interactive visualization allows for insights into cellular data encoded in MIF images but that typically require arduous manual analysis and effort because an MIF image may depict millions of cells. The graph embeddings provide information about each cell as well the neighborhood surrounding that cell and cellular relationships (similarities between cells, differences between cells, cell clusters, temporal information) which in turn may be provided in an interactive and visual manner. Because it shows interactions at the cell and cellular neighborhood level, the interactive visualization enables advanced hypothesis and data-driven research based on the MIF images in a number of possible uses including understanding cellular mechanisms with regard to cellular responses to different medical treatments and with regard to different responses and outcomes across different patients.

Process flow 100 will now be discussed in further detail with respect to FIGS. 2A, 2B and 3-5.

FIG. 2A illustrates an example multiplex immunofluorescence (MIF) system pipeline 200A for processing an MIF image, according to some embodiments. MIF system pipeline 200A may be implemented as part of a computer system, such as computer system 500 in FIG. 5. MIF system pipeline 200A may include various components for processing an MIF image and providing an interactive visualization of the MIF image. As shown in FIG. 2A, MIF system pipeline 200A may include MIF image analyzer 202A, graph generator 204A, embeddings generator 206A, and visualizer 208A.

MIF image analyzer 202A analyzes MIF images to identify cells within the images, extracts information from the MIF images, and converts the information to tabular data. In an embodiment, MIF image analyzer 202A may use software to perform the conversion to tabular data. Examples of such software include digital pathology platforms for quantitative tissue analysis.

The tabular data may include coordinates and properties of each cell. Coordinates of a cell may identify the location of the cell within the MIF image and may be used in plotting the cell with respect to other cells in the MIF image. In an embodiment, the coordinates may be implemented as X/Y coordinates. The coordinates may be based on different aspects of the cell. For example, MIF image analyzer 202A may identify a cell nucleus for the cell and the center of the cell nucleus may be used as the X/Y coordinate for the cell. As another example, the whole cell may be used as the X/Y coordinate.

The tabular data may further include other information extracted from the MIF images such as properties of the cell. A collection of cell properties may also be characterized as the cell phenotype and these properties may include any number of auxiliary features of the cell as determined from the image analysis performed by MIF image analyzer 202A. These auxiliary features may include the diameter of the cell, size of the cell, eccentricity of the cell, cell membrane, cytoplasm of the cell, and biomarker positivity of the cell. Each cell in the MIF image may be associated with an immunofluorescence intensity. In an embodiment, MIF image analyzer 202A may also normalize the immunofluorescence intensities identified within the MIF image. The normalization may be performed via a batch normalization of batches of immunofluorescence intensities. A batch may represent a subset of the plurality of immunofluorescence intensities identified in the MIF image. The immunofluorescence intensities may be used as input for training a graph and batch normalization of the intensities helps to improve the efficiency of the training by standardizing the intensities. In an embodiment, MIF image analyzer 202A may also normalize the auxiliary features to generate normalized auxiliary features.

In an embodiment, the image analysis involves segmenting portions of the image and labeling the segmented portions based on biological regions. For example, in an MIF image involving cancerous tissue, MIF image analyzer 202A may identify, based on characteristics of the cells in the image, cells in the image that correspond to a tumor center or tumor stroma.

Based on the coordinates and properties identified by MIF image analyzer 202A, graph generator 204A may generate a graph representative of the MIF image. The generated graph may include nodes corresponding to cells identified in the MIF image. The number of nodes may correspond directly with the number of cells identified in the MIF image. The generated graph may also include edges connecting a number of the nodes. Nodes connected by edges may be based on a selectable distance threshold (e.g., 10 microns) where nodes within the distance threshold are connected by edges in the graph and nodes outside the distance threshold are not. In an embodiment, graph generator 204A may perform pairwise modeling between cells by identifying node pairs based on the distance threshold and establishing edges between node pairs based on a distance between the nodes. Distances between nodes in the graph may be calculated by determining distances between coordinates associated with corresponding cells and based on whether the distances are within the predetermined threshold.

In an embodiment, the distance threshold may be determined based on the cell types of cells in the MIF image. It may be known that certain cell types have specific interactions within a particular distance. If those cell types are identified in the MIF image, the distance threshold may be selected based that particular distance. In an embodiment, there may be different distance thresholds established when constructing the graph. For example, if cell type A and cell type B are known to have interactions within 10 microns and cell type A and cell type C are known to have interactions within 20 microns, then graph generator 204A may utilize these different distances when determining whether to connect nodes in the graph. Accordingly, in this example, a node corresponding to cell type A may be connected to a node corresponding to cell type B only when the nodes are within 10 microns. A node corresponding to cell type A may be connected to a node corresponding to cell type C only when the nodes are within 20 microns.

In an embodiment, the distance threshold may be determined based on biomarkers of the cells in the MIF image. For example, there may be a different threshold for every pair of biomarkers within the cell.

The generated graph shows the pairwise relationship between nodes and provides a graphical representation of the cells identified in the MIF image. The connectivity of nodes in the graph may be used to characterize cellular neighborhoods.

In an embodiment, graph generator 204A may perform a sub-sampling step prior to the graph being transformed into embeddings by embeddings generator 206A. Sub-sampling may involve segmenting the graph into multiple sub-graphs and then feeding one or more of the sub-graphs (instead of the entire graph) to embeddings generator 206A. Sub-sampling the graph may be performed to improve the efficiency of calculating the embeddings by allowing embeddings generator 206A to work with a smaller portion of the graph. For example, the entire graph may not be relevant so the embeddings may be generated based only on the sub-graphs of interest.

Embeddings generator 206A trains the graph embeddings (or sub-graph embeddings if the graph has been sub-sampled) in order to generate embeddings which are mathematical vector representations of the information in the graph including information about each node (e.g., X/Y coordinates, biomarker expression) and each node's neighborhood (e.g., a certain subset of nodes that are within a certain distance from each node). In an embodiment, a graph training algorithm is applied to the graph in order to train the graph embeddings. The algorithm may entail selecting nodes from the graph and selecting a number of hops associated with each of the selected nodes. The number of hops defines a neighborhood around a node within the graph with each selected node as the center of each neighborhood and the number of hops representing the maximum number of consecutively traversable edges. In this manner, each neighborhood is a subset of nodes that includes the selected nodes and any nodes that are within the number of hops to the selected nodes. The algorithm may also entail selecting an embedding size which represents the amount of information associated with the graph that is preserved within each embedding. In an embodiment, the embedding size is a fixed-length mathematical vector such as 32 or 64 values.

In an embodiment, the selected nodes and selected number of hops are inputs to tunable aggregation functions. When generating an embedding for a selected node, aggregation functions pull embedding information from surrounding nodes and use the pulled embedding information to generate the embedding for the selected node. Accordingly, the aggregation functions enable each embedding to be a numerical representation of a node and its surrounding nodes (depending on the selected number of hops).

In an embodiment, the graph training algorithm is an unsupervised algorithm such as DGI or Graph-Sage. Hyper-parameters associated with the graph training algorithm may be selected so that the generated embeddings provide an accurate representation of the nodes in the graph. Examples of relevant hyper-parameters for application of the graph training algorithm include learning rate, dropout, optimizer, weight-decay, and edge-weighting. Tuning values for hyper-parameters ensures that the graph training algorithm will generate accurate embeddings representative of the graph. The result of the graph training algorithm are the embeddings for each node in the graph.

The embeddings may also include the normalized auxiliary features if auxiliary features have been extracted from the MIF image by MIF image analyzer 202A. Each cell identified in the MIF image has a corresponding embedding and each embedding encodes all the information about the cell in a numerical format. An example of an embedding is a vector. The embedding for a node may be generated based on embedding information from a certain number of nodes surrounding that node. In this manner the embedding for a node captures information about the node and for its neighborhood.

The embeddings may also encode temporal information associated with each cell. For example, the temporal information may relate to characteristics of the cell at different points of a medical treatment (e.g., dose two at week four, dose four at week six) or progression of a particular disease (e.g., patient's kidney at week one, patient's kidney at week two). Characteristics of the cell such as size or eccentricity may indicate how the cell is reacting to the medical treatment or progressing in the disease. As an example, the size of a cell at a second dose of a medical treatment may be compared to the size of the cell at a fourth dose of the medical treatment. The variation in size (e.g., increase, decrease, no change) could be encoded in the embeddings.

Visualizer 208A provides an interactive visualization of the graph based on the embeddings generated by embeddings generator 206A. Visualizer 208A may reduce the dimensionality of the embeddings to two, or three, dimensions so that the information of the embeddings may be displayed visually, such as on a graph, in the interactive visualization.

The interactive visualization may be populated with a number of selectable icons that are a visual representation of the numerical information provided in the embeddings. The interactive visualization is a user interface that may display the selectable icons and allow for interaction with the selectable icons. The placement and visual configuration of the icons is based on the embeddings. Each selectable icon in the interactive visualization therefore may be considered to correspond to a particular node in the graph generated by graph generator 204A as well as that particular node's neighborhood. In an embodiment, the interactive visualization is a two-dimensional representation of the embeddings.

Visual properties of the selectable icons may be adjusted to reflect different information encoded in the embeddings. Selectable icons may be different colors, different sizes, different shapes, or different borders, and each of these properties may be configured to reflect a particular property of the embedding and its corresponding node in the graph. For example, colors of icons may be used to reflect different cell phenotypes (e.g., a blue icon may be associated with cell phenotype A while a red icon may be associated with cell phenotype B) while borders of the icons may be used to reflect biomarkers associated with the cells (e.g., a thick border may be associated with biomarker A while a thin border may be associated with biomarker B). Functions of the interactive visualization may include allowing selection of the selectable icons, querying, filtering, plotting/graphing the embeddings, generating neighborhood graphs, and generating statistical summaries. A user may use a cursor to lasso or draw a box over icons to provide a selection of a subset of the selectable icons. The selected subset of selectable icons represents a cell neighborhood that corresponds to the embeddings associated with the selectable icons. The interactive visualization may provide a graphical plot that includes the subset of the selectable icons where the plot may be configured to represent the cell neighborhood. The graphical plot may display information about the selected subset including highlighting the selected cells in the subset, an infographic with details about each of the selected cells, and other information provided in the embeddings of the selected cells. The infographic may include biomarker information, temporal information, and labeling information.

In an embodiment, when temporal information is encoded in the embeddings, the interactive visualization may provide information regarding the characteristics of each cell at different points in time such as different medical treatments and different weeks. The interactive visualization may provide a filter that allows selection of these different times and allows for comparison of the cells at those selected times.

Figure 2B:
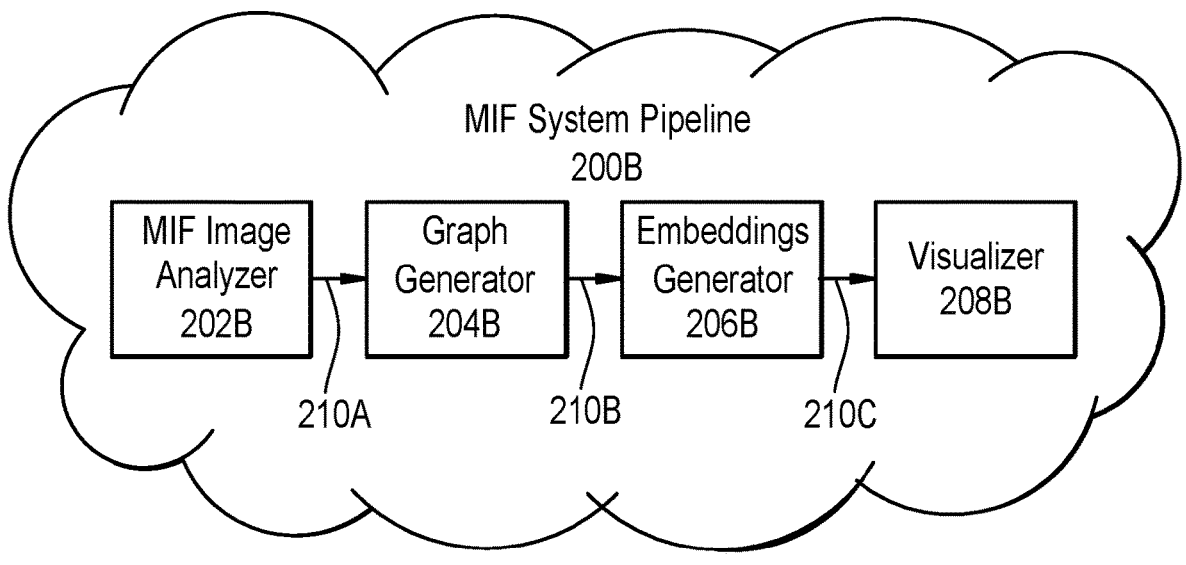
FIG. 2B illustrates an alternative embodiment of the example multiplex immunofluorescence image system pipeline.

FIG. 2B illustrates an embodiment of MIF system pipeline 200B for processing an MIF image that may be distributed across multiple computers in a network or a cloud-based environment. For example, MIF system pipeline 200B may be implemented as part of a cloud-based environment and each component of MIF system pipeline 200B distributed between multiple computers connected to each other in the environment. MIF system pipeline 200B may include MIF image analyzer 202B, graph generator 204B, embeddings generator 206B, and visualizer 208B. These components may perform the same functionality as the respective components of MIF system pipeline 200A, described above, but implemented in the same or different computers and connected within MIF system pipeline 200B via network connections 210A-C within the network or cloud-based environment.

In some embodiments, MIF image analyzer 202B, graph generator 204B, embeddings generator 206B, and visualizer 208B may be implemented on different computers. MIF image analyzer 202B may communicate the results of its image analysis to graph generator 204B via a network connection 210A. Similarly, graph generator 204B may communicate a trained graph generated based on the results of the image analysis to embeddings generator 206B via network connection 210B. And the embeddings generator

206B may communicate the embeddings generated from the trained graph to the visualizer 208B via network connection 210C.

In some embodiments, one or more components may be implemented on the same devices within the network or cloud-based network. For example, MIF image analyzer 202B may be implemented on the same device as graph generator 204B while embeddings generator 206B may be implemented on the same device as visualizer 208B.

Figure 4A:
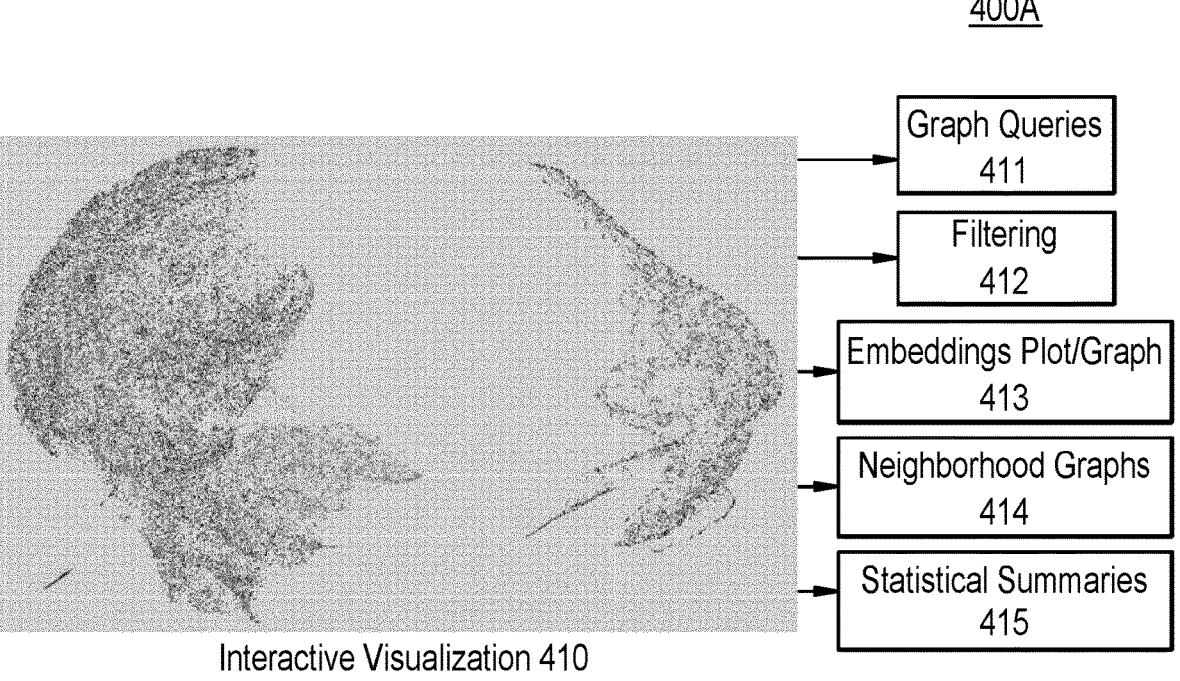
FIG. 4A illustrates an example process flow for utilizing an interactive visualization of a multiplex immunofluorescence image, according to some embodiments.
Figure 4B:
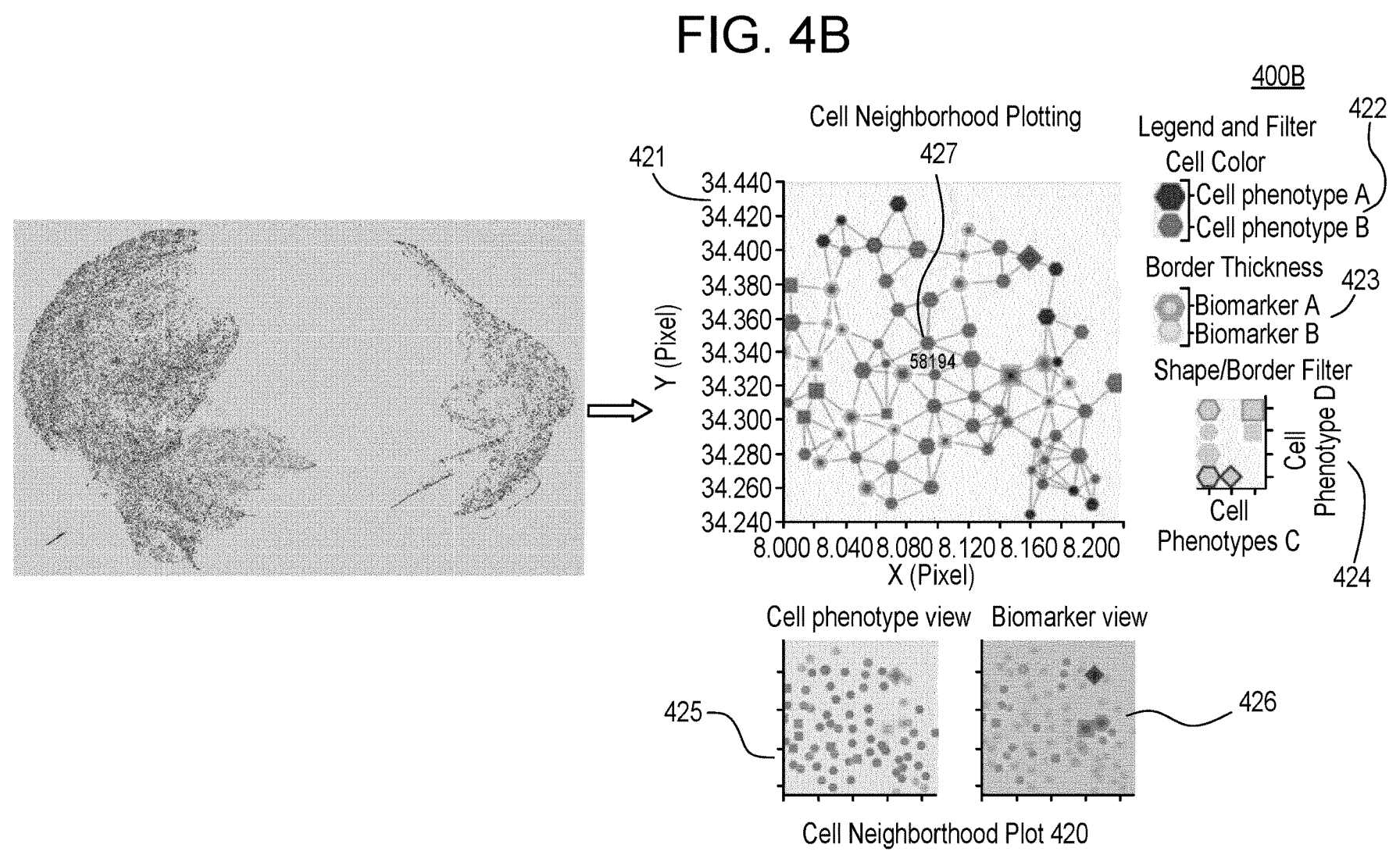

The interactive visualization is discussed in additional detail in FIGS. 4A and 4B.

FIG. 3 illustrates an example method 300 for providing an interactive visualization of a multiplex immunofluorescence image, according to some embodiments. As a non-limiting example with reference to FIG. 2, one or more processes described with respect to FIG. 3 may be performed by an MIF system (e.g., MIF system pipeline 200 of FIG. 2) to transform an MIF image into an interactive visualization of the cellular environment depicted in the MIF image. In such an embodiment, MIF system pipeline 200 may execute code in memory to perform certain steps of method 300. While method 300 will be discussed below as being performed by MIF system pipeline 200, other devices may store the code and therefore may execute method 300 by directly executing the code. Accordingly, the following discussion of method 300 refers to FIG. 2 merely as an exemplary non-limiting embodiment of method 300. For example, method 300 may be executed on any computing device, such as, for example, the computer system described with reference to FIG. 5 and/or processing logic that may comprise hardware (e.g., circuitry, dedicated logic, programmable logic, microcode, etc.), software (e.g., instructions executing on a processing device), or a combination thereof. Moreover, it is to be appreciated that not all steps may be needed to perform the disclosure provided herein. Further, some of the steps may be performed simultaneously or in a different order than shown in FIG. 3, as will be understood by a person of ordinary skill in the art.

In 310, MIF image analyzer 202 performs image analysis on the MIF image, which includes identifying cells within the MIF image. The result of this analysis is tabular data that represents information about each identified cell.

In 320, MIF image analyzer 202 may extract cell coordinates and biomarker information from the tabular data. In some embodiments, the cell coordinates may include X/Y coordinates of each cell and the biomarker information may include immunofluorescence intensities associated with every cell. In some embodiments, the extracted information may further include the auxiliary features discussed above.

In 330, graph generator 204 constructs the graph based on the extracted information. In some embodiments, graph generator 204 may construct the graph with information about each node where the nodes in the graph correspond to cells identified in the image. The graph facilitates detection of the cellular relationships in the image by representing the image data as more easily processed information about each identified cell in the image. In some embodiments, the graph connects nodes based on a distance threshold and the size of a neighborhood within the graph is defined by the number of hops from a particular node. For example, if the number of hops is set to three, then the neighborhood of a particular node includes all nodes within the graph that are three hops (or connections) from that node. At this stage, each node in the graph includes information corresponding to a single cell in the MIF image.

In 340, embeddings generator 206 trains the graph and generates embeddings from the trained graph. Training the graph results in each node including information about a corresponding cell as well as that cell's neighborhood. Different machine learning algorithms may be utilized to train the graph. In some embodiments, embeddings generator 206 may utilize an unsupervised or self-supervised machine learning algorithm to train the graph which utilizes unlabeled data to identify the embeddings in the current graph. In contrast, in other embodiments, embeddings generator 206 may utilize a supervised machine learning algorithm which utilizes a previously labelled graph to train the current graph and identify embeddings based on the previously labelled graph.

In embodiments that utilize an unsupervised or self-supervised machine learning algorithm, embeddings generator 206 may utilize association rules to discover patterns or relationships between the features of neighboring cells (also referred to as "nodes") within a predefined distance threshold. There may be trainable parameters in a trainable weights matrix applied to the features, for example, but there is no target prediction defined by a previously labelled graph. An advantage of unsupervised or self-supervised machine learning in these embodiments is that a greater quantity of unlabeled data can be leveraged for pre-training, so that embeddings generated for a target graph will be likely to contain more useful domain information.

In embodiments that utilize a supervised machine learning algorithm, embeddings generator 206 may utilize classification algorithms to recognize and group cells based on a previously labelled graph or data. An advantage of supervised machine learning in these embodiments is that the classification of nodes may be more accurate and the graph can be trained to meet specific classifications (based on the previously labelled data).

Embeddings are generated to capture information about every cell identified in the MIF image as well as neighboring cells. The nodes in the graph represent the cell and associated information including biomarker expression for the cell. Every node is associated with an embedding that encodes information about the cell and its neighborhood (which is defined by the selectable number of hops from the cell). For example, information about the cell and its neighbors—such as features of the cell, features of neighboring cells, identification of neighboring cells, and the connecting structures—may be aggregated together into a single feature vector using a trainable weights matrix. In some embodiments, this feature vector constitutes an embedding.

In 350, visualizer 208 generates the interactive visualization populated with selectable icons based on the embeddings. The interactive visualization provides an interface for receiving inputs that manipulate the selectable icons. Visualizer 208 may apply a learning technique that reduces the dimensionality of the embeddings. In an embodiment, the embeddings may be reduced to a two-dimensional visual representation (such as a plot). Current examples of this learning technique include Uniform Manifold Approximation and Projection (UMAP) and t-distributed stochastic neighbor embedding (t-SNE). Visualizer 208 may, in some cases, sub-sample embeddings that are used to generate the visualization in cases where it would be impractical to execute the dimensionality reduction algorithm on all embeddings due to computational complexity. The sub-sampling algorithm may be random, stratified random, or any alternate approach.

In 360, MIF system pipeline 200 may additionally feed the embeddings to a machine learning algorithm of a neural network to generate a predictive model for treatment response and survival prediction. An output of the machine learning algorithm may be a prediction about how a patient may respond to a particular treatment (at the cellular level) or a likelihood of survival. Information, including any temporal information, in the embeddings may be used as inputs to the machine learning algorithm. In an embodiment, the machine learning algorithm is supervised. The embeddings may be provided as an input to the neural network which may generate, based on the embeddings, a prediction associated with the cells identified in the MIF image. In an embodiment, the prediction relates to a predicted medical or treatment outcome associated with the cells. For example, the MIF image may depict cancerous cells and the machine learning algorithm may utilize the embeddings to predict an outcome of the cells. The prediction may take the form of an updated interactive visualization with the visual properties of the selectable cells updated to reflect the predicted outcome. In other words, the MIF image may depict cells that are associated with a medical condition and the predicted outcome is for the medical condition. In another embodiment, the prediction may relate to a predicted response associated with the plurality of cells. For example, the MIF image may depict cells being treated for cancer and the machine learning algorithm may utilize the embeddings to predict how the cells may respond to the treatment. The prediction may take the form of an updated interactive visualization with the visual properties of the selectable cells updated to reflect the predicted treatment response. In other words, the MIF image may depict cells associated with a medical condition and the predicted response is for a patient response to a treatment for the medical condition.

In an embodiment, applying the machine learning algorithm may involve selecting an embedding aggregation strategy, or how the information, including the temporal information, in the embeddings are to be processed into a single vector representation. Examples of a strategy include taking an average of the embedding information, providing a per cell prediction, providing a prediction based on region-of-interest (or a group of cells), or taking an average or maximum of a grid of cells. In another embodiment, the machine learning algorithm may involve a multi-layer perceptron (MLP) classifier or a convolutional neural network.

In an embodiment, performance of the predictive model may be evaluated by comparing the predictions with actual outcomes or patient response. For example, a prediction of patient response to a particular medical treatment may be compared with the actual response and this comparison may be used to further tune the predictive model to improve accuracy.

FIG. 4A illustrates an example process flow 400A for utilizing interactive visualization 410 of a multiplex immunofluorescence image, according to some embodiments.

Interactive visualization 410 may provide an interface for graph queries 411. In an embodiment, graph queries 411 may involve receiving, as input, a graph query associated with the nodes in the graph. Queries may be focused on searching for particular cells or cell neighborhoods within a graph that fit a search criteria. The query may involve a parameter or a threshold value for identifying nodes in the graph. For example, a query may be used to search for cells with cell neighborhoods having certain biomarkers expressed by over a threshold value of 50% of cells. Graph queries 411 may result in displaying the result of the query, such as the cells or cell neighborhoods that match the query. In an embodiment, the matching cells or cell neighborhoods may be highlighted in interactive visualization 410.

Interactive visualization 410 may also provide an interface for performing filtering 412 which may include data parameters for filtering the selectable icons in interactive visualization 410. Examples of parameters include whole slide imaging (WSI), patient, label, and temporal information such as pre-operation/post-operation and response to treatment. Parameters may be provided via a drop-down box. Interactive visualization 410 filters the selectable icons by displaying only the selectable icons that match the selected options. For example, a particular digital file (WSI) may be selected, a particular patient (or patients), one or more labels that have been assigned the nodes in the graph, labels identifying cells from pre-operation patients, labels identifying cells from post-operation patients, labels identifying cells from pre-treatment patients, labels identifying cells from post-treatment patients, response labels identifying patients that did or did not respond to a particular treatment, just to name a few examples. Each of these parameters may have additional sub-options. For example, patients may be segmented into different categories such as patients who responded to a particular treatment and patients who did not respond.

Interactive visualization 410 may also provide an interface for plotting or graphing embeddings 413 which involves down-projecting the embeddings to a two-dimensional plot and feeding the two-dimensional plot to the interface that can receive user input for manipulation and interaction. Icons in the two-dimensional plot (which correspond to the nodes in the graph represented by the embeddings) may be visually configured to represent properties of the cell and its neighborhood. Examples include different colors, different shapes, and different sizes. In an embodiment, icons may be configured so that the interface provides a heatmap (e.g., changes in color) to represent temporal information for the corresponding cells. For example, the heatmap may be used to illustrate changes to cells from pre-operation to post-operation. The interface allows for box/lasso selection inputs for selecting subsets of the selectable icons. The interface may also allow gradients on the plot to be highlighted indicating temporal information or cell-neighborhood heterogeneity. The interface may also provide an option for a user to submit commands to manipulate a grouping of icons in interactive visualization 410 such as panning, rotating about an axis, and, zooming into a particular cell or cell neighborhood.

Interactive visualization 410 may also provide an interface for graphing cellular neighborhoods 414. After a selection of a subset of the selectable icons (e.g., via box/lasso selection), identifiers of the corresponding cells may be determined based on the embeddings associated with the selected subset. These identifiers may be used to generate a plot of the cellular neighborhood or neighborhoods for the selected subset. In an embodiment, graphing cellular neighborhoods 414 may configure the neighborhood plot to use different visual properties (e.g., border, color, shape) to represent the selectable icons based on the corresponding biomarkers (or other cellular information) for the cells corresponding to the icons depicted in interactive visualization 410.

An example of a cellular neighborhood plot is described with respect to FIG. 4B.

Interactive visualization 410 may also provide an interface for generating statistical summaries 415. After receiving a selection of selectable icons from interactive visualization 410 (e.g., a box/lasso selection), the interface may generate statistical summaries associated with the selected icons. For example, the interface may report the number of cells with immunofluorescence intensity above a certain threshold in the selection. The interface may also report the proportion of icons within the selection exceeding the threshold for each biomarker. In another embodiment, the interface may report the average immunofluorescence intensity per biomarker for the selected icons.

Other examples of statistical summaries include a reporting on a proportion and count of biomarkers, providing a sub-graph (e.g., cellular neighborhood) density, ranking biomarker vectors/cell phenotypes based on prevalence within the selected icons (e.g., showing count and/or proportion), providing a temporal report such as a summary to show before and after images of the selected icons (e.g. comparing previous cellular information with current cellular information), and providing comparisons between neighborhoods such as by highlighting changes in neighborhood biomarker expression, neighborhood density, or cell phenotype.

FIG. 4B illustrates an example process flow 400B for generating cell neighborhood plot 420 from interactive visualization 410 of a multiplex immunofluorescence image, according to some embodiments.

Cell neighborhood plot 420 may include a plot 421 showing a neighborhood around target cell 427 and a legend providing information regarding the visual indicators of the icons in the plot. In this embodiment, the number of hops is any selectable value from one to six which represents all cells within one to six hops from target cell 427. The visual indicators may indicate the properties of the corresponding cell. For example, the legend may associate cell color 422 with a cell phenotype, border thickness 423 with biomarker information, and shape/border filter 424 with multiple cell phenotypes.

Icons in cell neighborhood plot 421 may also be interactive and selectable. As with icons in interactive visualization 410, icons in cell neighborhood plot 421 also correspond to a particular trained embedding (indicating a cell and its surrounding neighborhood). Interacting with the icon may provide information about the corresponding node and the neighborhood.

Cell neighborhood plot 420 may also provide views based on filtering the visual indicators such as a cell phenotype view 425 or a biomarker view 426.

Example Computer System

Figure 5:
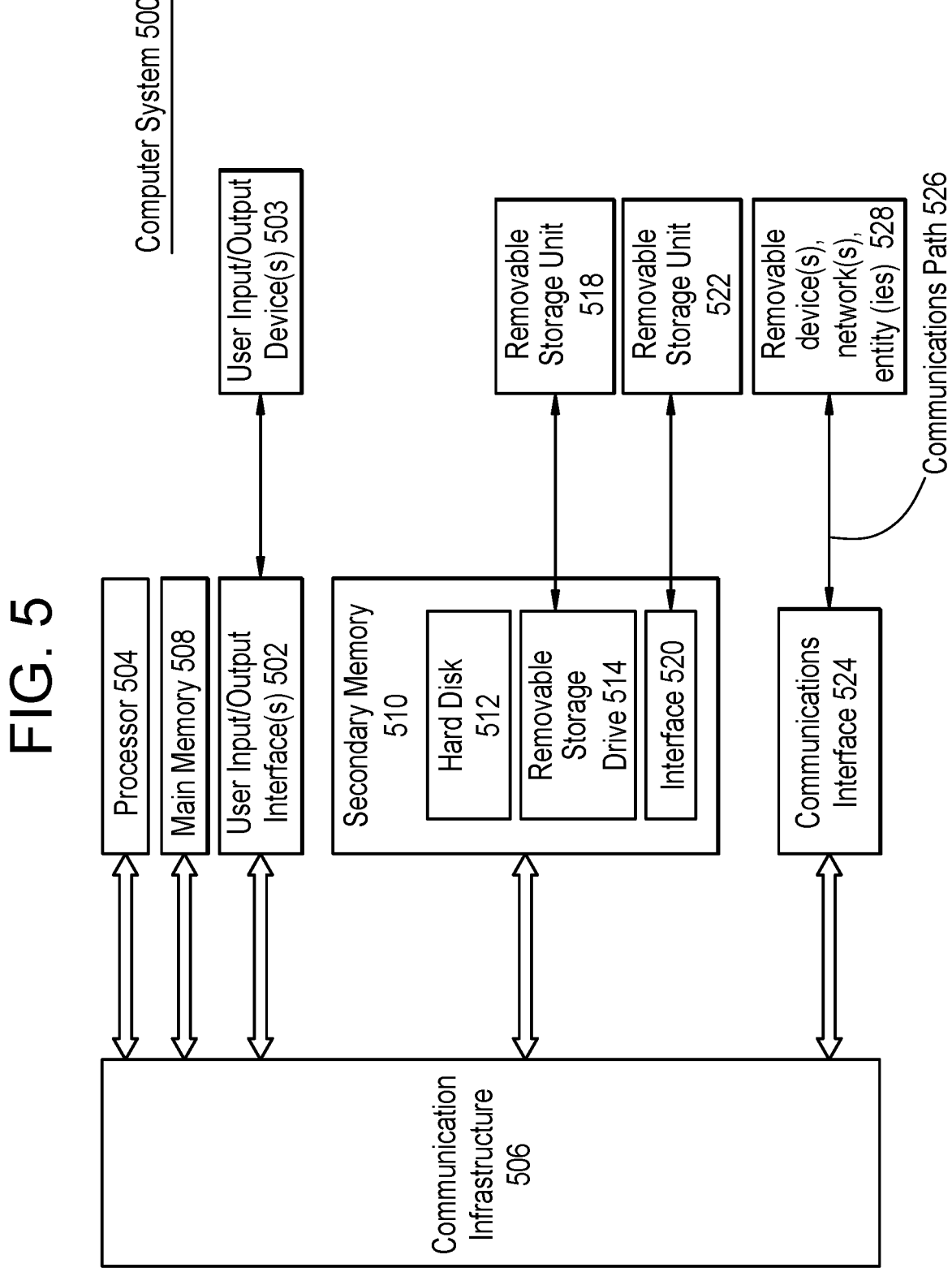
FIG. 5 illustrates an example computer system useful for implementing various embodiments.

Various embodiments and/or components described herein can be implemented, for example, using one or more computer systems, such as computer system 500 shown in FIG. 5. Computer system 500 can be any computer or computing device capable of performing the functions described herein. For example, one or more computer systems 500 can be used to implement any embodiments of FIGS. 1-4, and/or any combination or sub-combination thereof.

The following example computer system, or multiple instances thereof, may be used to implement methods 300 of FIG. 3, respectively, systems as shown in FIG. 2, or any component thereof, according to some embodiments.

Various embodiments may be implemented, for example, using one or more well-known computer systems, such as computer system 500 shown in FIG. 5. One or more computer systems 500 may be used, for example, to implement any of the embodiments discussed herein, as well as combinations and sub-combinations thereof.

Computer system 500 may include one or more processors (also called central processing units, or CPUs), such as a processor 504. Processor 504 may be connected to a bus or communication infrastructure 506.

Computer system 500 may also include user input/output device(s) 505, such as monitors, keyboards, pointing devices, etc., which may communicate with communication infrastructure 506 through user input/output interface(s) 502.

One or more of processors 504 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, vector processing, array processing, etc., as well as cryptography, including brute-force cracking, generating cryptographic hashes or hash sequences, solving partial hash-inversion problems, and/or producing results of other proof-of-work computations for some blockchain-based applications, for example. With capabilities of general-purpose computing on graphics processing units (GPGPU), the GPU may be particularly useful in at least the feature-extraction and machine-learning aspects described herein.

Additionally, one or more of processors 504 may include a coprocessor or other implementation of logic for accelerating cryptographic calculations or other specialized mathematical functions, including hardware-accelerated cryptographic coprocessors. Such accelerated processors may further include instruction set(s) for acceleration using coprocessors and/or other logic to facilitate such acceleration.

Computer system 500 may also include a main or primary memory 508, such as random access memory (RAM). Main memory 508 may include one or more levels of cache. Main memory 508 may have stored therein control logic (i.e., computer software) and/or data.

Computer system 500 may also include one or more secondary storage devices or secondary memory 510. Secondary memory 510 may include, for example, a main storage drive 512 and/or a removable storage device or drive 514. Main storage drive 512 may be a hard disk drive or solid-state drive, for example. Removable storage drive 514 may be a floppy disk drive, a magnetic tape drive, a compact disk drive, an optical storage device, tape backup device, and/or any other storage device/drive.

Removable storage drive 514 may interact with a removable storage unit 518. Removable storage unit 518 may include a computer usable or readable storage device having stored thereon computer software (control logic) and/or data. Removable storage unit 518 may be a floppy disk, magnetic tape, compact disk, DVD, optical storage disk, and/any other computer data storage device. Removable storage drive 514 may read from and/or write to removable storage unit 518.

Secondary memory 510 may include other means, devices, components, instrumentalities or other approaches for allowing computer programs and/or other instructions and/or data to be accessed by computer system 500. Such means, devices, components, instrumentalities or other approaches may include, for example, a removable storage unit 522 and an interface 520. Examples of the removable storage unit 522 and the interface 520 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 500 may further include a communication or network interface 524. Communication interface 524 may enable computer system 500 to communicate and interact with any combination of external devices, external networks, external entities, etc. (individually and collectively referenced by reference number 528). For example, communication interface 524 may allow computer system 500 to communicate with external or remote devices 528 over communication path 526, which may be wired and/or wireless (or a combination thereof), and which may include any combination of LANs, WANs, the Internet, etc. Control logic and/or data may be transmitted to and from computer system 500 via communication path 526.

Computer system 500 may also be any of a personal digital assistant (PDA), desktop workstation, laptop or notebook computer, netbook, tablet, smart phone, smart watch or other wearable, appliance, part of the Internet of Things (IoT), and/or embedded system, to name a few non-limiting examples, or any combination thereof.

Computer system 500 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), database as a service (DBaaS), etc.); and/or a hybrid model including any combination of the foregoing examples or other services or delivery paradigms.

Any applicable data structures, file formats, and schemas may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

Any pertinent data, files, and/or databases may be stored, retrieved, accessed, and/or transmitted in human-readable formats such as numeric, textual, graphic, or multimedia formats, further including various types of markup language, among other possible formats. Alternatively or in combination with the above formats, the data, files, and/or databases may be stored, retrieved, accessed, and/or transmitted in binary, encoded, compressed, and/or encrypted formats, or any other machine-readable formats.

Interfacing or interconnection among various systems and layers may employ any number of mechanisms, such as any number of protocols, programmatic frameworks, floorplans, or application programming interfaces (API), including but not limited to Document Object Model (DOM), Discovery Service (DS), NSUserDefaults, Web Services Description Language (WSDL), Message Exchange Pattern (MEP), Web Distributed Data Exchange (WDDX), Web Hypertext Application Technology Working Group (WHATWG) HTML5 Web Messaging, Representational State Transfer (REST or RESTful web services), Extensible User Interface Protocol (XUP), Simple Object Access Protocol (SOAP), XML Schema Definition (XSD), XML Remote Procedure Call (XML-RPC), or any other mechanisms, open or proprietary, that may achieve similar functionality and results.

Such interfacing or interconnection may also make use of uniform resource identifiers (URI), which may further include uniform resource locators (URL) or uniform resource names (URN). Other forms of uniform and/or unique identifiers, locators, or names may be used, either exclusively or in combination with forms such as those set forth above.

Any of the above protocols or APIs may interface with or be implemented in any programming language, procedural, functional, or object-oriented, and may be compiled or interpreted. Non-limiting examples include C, C++, C#, Objective-C, Java, Swift, Go, Ruby, Perl, Python, JavaScript, WebAssembly, or virtually any other language, with any other libraries or schemas, in any kind of framework, runtime environment, virtual machine, interpreter, stack, engine, or similar mechanism, including but not limited to Node.js, V8, Knockout, j Query, Dojo, Dijit, OpenUI5, AngularJS, Express.js, Backbone.js, Ember.js, DHTMLX, Vue, React, Electron, and so on, among many other non-limiting examples.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 500, main memory 508, secondary memory 510, and removable storage units 518 and 522, as well as tangible articles of manufacture embodying any combination of the foregoing. Such control logic, when executed by one or more data processing devices (such as computer system 500), may cause such data processing devices to operate as described herein.

Based on the teachings contained in this disclosure, it will be apparent to persons skilled in the relevant art(s) how to make and use embodiments of this disclosure using data processing devices, computer systems and/or computer architectures other than that shown in FIG. 5. In particular, embodiments may operate with software, hardware, and/or operating system implementations other than those described herein.

<div align="center">CONCLUSION</div>

It is to be appreciated that the Detailed Description section, and not any other section, is intended to be used to interpret the claims. Other sections may set forth one or more but not all exemplary embodiments as contemplated by the inventor(s), and thus, are not intended to limit this disclosure or the appended claims in any way.

While this disclosure describes exemplary embodiments for exemplary fields and applications, it should be understood that the disclosure is not limited thereto. Other embodiments and modifications thereto are possible, and are within the scope and spirit of this disclosure. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries may be defined as long as the specified functions and relationships (or equivalents thereof) are appropriately performed. Also, alternative embodiments may perform functional blocks, steps, operations, methods, etc. using orderings different from those described herein.

References herein to "one embodiment," "an embodiment," "an example embodiment," "some embodiments," or similar phrases, indicate that the embodiment described may include a particular feature, structure, or characteristic, but every embodiment may not necessarily include the particular feature, structure, or characteristic. Moreover, such phrases are not necessarily referring to the same embodiment.

Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein. Additionally, some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

The breadth and scope of this disclosure should not be limited by any of the above-described exemplary embodiments, but should be defined only in accordance with the following claims and their equivalents.

What is claimed is:

1. A method for characterizing a cell interaction from a multiplex immunofluorescence image, the method comprising:

identifying a plurality of cells in the multiplex immunofluorescence image, wherein each cell in the plurality of cells is associated with a respective coordinate and respective properties, the plurality of cells including at least a first cell and a second cell;

generating a graph of the multiplex immunofluorescence image based on the respective coordinates and the respective properties of the plurality of cells, wherein:

the graph includes a plurality of nodes corresponding to respective cells of the plurality of cells and a plurality of edges that connect respective pairs of nodes, the plurality of nodes includes at least a first node corresponding to the first cell and a second node corresponding to the second cell, and the plurality of edges includes at least an edge between the first node and the second node;

transforming the graph into a plurality of embeddings, wherein the plurality of embeddings includes node embeddings for the plurality of nodes corresponding to the respective cells of the plurality of cells;

using a dimensionality-reduction technique to reduce a dimensionality of the node embeddings to either two or three dimensions; and providing an interactive visualization comprising a plurality of selectable icons that each represents a respective reduced-dimensionality node embedding for a respective node corresponding to a respective cell of the plurality of cells.

2. The method of claim 1, further comprising:

generating normalized immunofluorescence intensities for the plurality of cells using a batch normalization of a batch of immunofluorescence intensities, wherein the respective properties for the plurality of cells include the normalized immunofluorescence intensities.

3. The method of claim 1, wherein generating the graph comprises:

detecting a plurality of node pairs for the plurality of cells, wherein the plurality of node pairs includes the first node and the second node as a pair of nodes; and establishing the edge between the first node and the second node based on a distance between the respective coordinates of the first and second nodes being within a predetermined threshold.

4. The method of claim 1, further comprising:

extracting an auxiliary feature of the first cell, wherein the auxiliary feature includes at least one of a diameter of the first cell, an area of the first cell, or an eccentricity of the first cell.

5. The method of claim 4, further comprising:

generating normalized auxiliary features using a normalization of a plurality of auxiliary features of the plurality of cells including the auxiliary feature of the first cell, wherein the plurality of embeddings are generated based in part on the normalized auxiliary features.

6. The method of claim 1, wherein transforming the graph into the plurality of embeddings comprises:

selecting a number of hops that defines a neighborhood of a selected node within the graph, wherein the neighborhood of the respective node comprises a subset of the plurality of nodes including the selected node and any nodes of the plurality of nodes within the number of hops to the selected node; and selecting an embedding size that defines an amount of information associated with the graph that is preserved within the plurality of embeddings.

7. The method of claim 6, wherein transforming the graph into the plurality of embeddings further comprises:

applying a machine learning algorithm to the graph based on the number of hops and the embedding size; and generating the plurality of embeddings based on applying the machine learning algorithm.

8. The method of claim 7, wherein the machine learning algorithm is an unsupervised graph training algorithm and wherein applying the machine learning algorithm to the graph is further based on at least one selected hyperparameter.

9. The method of claim 1, wherein the interactive visualization is configured to receive a selection of a subset of the plurality of selectable icons that represent reduceddimensionality node embeddings for a subset of nodes corresponding to a subset of the plurality of cells, and wherein the subset of the plurality of cells is associated with one or more cell neighborhoods, the method further comprising:

providing a graphical plot of the one or more cell neighborhoods.

10. The method of claim 1, wherein the interactive visualization is configured to perform at least one of the following:

receive a query regarding at least a subset of the respective properties for the plurality of nodes, wherein the query comprises a threshold value for identifying a subset of the plurality of nodes in the graph;

filter the plurality of selectable icons in the interactive visualization based on a data parameter, wherein the data parameter includes at least one of a patient, a response label, an image label, or a cell type;

receive a selection of the subset of the plurality of selectable icons in the interactive visualization;

receive a command to manipulate the interactive visualization; or provide a statistical summary of biomarkers or cell phenotypes associated with the plurality of selectable icons.

11. The method of claim 1, further comprising:

providing the plurality of embeddings as an input to a neural network; and generating, by the neural network, a prediction associated with the plurality of cells based on the plurality of embeddings, wherein the prediction is one of a predicted outcome associated with the plurality of cells or a predicted response associated with the plurality of cells.

12. The method of claim 11, wherein the multiplex immunofluorescence image is associated with a medical condition and the predicted outcome is for the medical condition.

13. The method of claim 11, wherein the multiplex immunofluorescence image is associated with a medical condition and the predicted response is for a patient response to a treatment for the medical condition.

14. The method of claim 1, further comprising:

prior to transforming the graph into the plurality of embeddings:

sub-sampling the graph into a plurality of sub-graphs; and transforming the plurality of sub-graphs into the plurality of embeddings.

15. A computing system, comprising:

at least one processor;

at least one non-transitory computer readable medium; and program instructions stored on the at least one non-transitory computer readable medium that, when executed by the at least one processor, cause the computing system to:

identify a plurality of cells in a multiplex immunofluorescence image, wherein each cell in the plurality of cells is associated with a respective coordinate and respective properties, the plurality of cells including at least a first cell and a second cell;

generate a graph of the multiplex immunofluorescence image based on the respective coordinates and the respective properties of the plurality of cells, wherein:

the graph includes a plurality of nodes corresponding to respective cells of the plurality of cells and a plurality of edges that connect respective pairs of nodes, the plurality of nodes includes at least a first node corresponding to the first cell and a second node corresponding to the second cell, and the plurality of edges includes at least an edge between the first node and the second node;

transform the graph into a plurality of embeddings, wherein the plurality of embeddings includes node embeddings for the plurality of nodes corresponding to the respective cells of the plurality of cells;

use a dimensionality-reduction technique to reduce a dimensionality of the node embeddings to either two or three dimensions; and provide an interactive visualization comprising a plurality of selectable icons that each represents a respective reduced-dimensionality node embedding for a respective node corresponding to a respective cell of the plurality of cells.

16. A non-transitory computer-readable device having instructions stored thereon that, when executed by at least one processor, cause a computing system to perform operations comprising:

identifying a plurality of cells in a multiplex immuno-fluorescence image, wherein each cell in the plurality of cells is associated with a respective coordinate and respective properties, the plurality of cells including at least a first cell and a second cell;

generating a graph of the multiplex immunofluorescence image based on the respective coordinates and the respective properties of the plurality of cells, wherein:

the graph includes a plurality of nodes corresponding to respective cells of the plurality of cells and a plurality of edges that connect respective pairs of nodes, the plurality of nodes includes at least a first node corresponding to the first cell and a second node corresponding to the second cell, and the plurality of edges includes at least an edge between the first node and the second node;

transforming the graph into a plurality of embeddings, wherein the plurality of embeddings includes node embeddings for the plurality of nodes corresponding to the respective cells of the plurality of cells;

using a dimensionality-reduction technique to reduce a dimensionality of the node embeddings to either two or three dimensions; and providing an interactive visualization comprising a plurality of selectable icons that each represents a respective reduced-dimensionality node embedding for a respective node corresponding to a respective cell of the plurality of cells.

17. The method of claim 1, wherein the dimensionality-reduction technique comprises either (i) a Uniform Manifold Approximation and Projection (UMAP) technique or (ii) a t-distributed stochastic neighbor embedding (t-SNE) technique.

18. The method of claim 1, wherein each respective node embedding represents information about the respective cell corresponding thereto that includes (i) the respective coordinate of the respective cell, (ii) at least a subset of the respective properties of the respective cell, and (iii) neighborhood information for the respective cell.

19. The method of claim 1, wherein the plurality of selectable icons each have visual properties that are determined based on the respective properties of the respective cell.

20. The method of claim 19, wherein the visual properties are determined based on the respective properties of the respective cell include at least one visual property that is determined based on a respective cell phenotype of the respective cell.

* * * * *